United States Patent [19]

Bishop

[11] 4,436,824
[45] Mar. 13, 1984

[54] LEUKOCYTE MIGRATION THROUGH ANTIGEN CONTAINING AGAROSES FOR IMMUNOCOMPETENCE TESTING

[75] Inventor: David C. Bishop, Sergeantsville, N.J.

[73] Assignee: Ortho Diagnostic Systems, Inc., Raritan, N.J.

[21] Appl. No.: 271,864

[22] Filed: Jun. 9, 1981

[51] Int. Cl.³ .................... G01N 33/48; G01N 33/50; G01N 33/54
[52] U.S. Cl. ............................... 436/514; 436/63; 436/64; 436/515; 436/519; 436/529; 436/808; 436/811; 436/813
[58] Field of Search .................. 436/514, 809, 63, 64, 436/515, 519, 529, 808, 811, 813; 435/7

[56] References Cited

U.S. PATENT DOCUMENTS

| | | | |
|---|---|---|---|
| 2,304,817 | 12/1942 | Grozin | 436/809 X |
| 3,941,876 | 3/1976 | Marinkovich | 436/809 X |
| 3,960,490 | 6/1976 | Giaever | 436/809 X |
| 3,969,497 | 7/1976 | Kniker | 436/514 X |
| 4,081,241 | 3/1978 | Porzsott | 436/514 X |
| 4,157,895 | 6/1979 | Finlay | 436/809 X |
| 4,254,219 | 3/1981 | Fullerton | 435/7 |
| 4,331,650 | 5/1982 | Brewer | 436/809 X |

OTHER PUBLICATIONS

Chemical Abstracts, 87:51441y (1977).
Chemical Abstracts, 88:35693x (1978).
J. E. Clausen, Acta Allergologica, 30, 239-249 (1975).
J. E. Clausen, Acta Allergologica, 31, 116-129 (1976).
Manual of Clinical Immunology, N. R. Rose and H. Friedman, et al., American Society of Microbiology, 1976, Chapter 6-L. E. Spitler.
F. K. Nkrumah, et al., Int. J. Cancer: 20, 6-11 (1977) and D. H. Char, et al., N.E.J. Med: 291 (6), 274-277 (1974).
Clausen (Danish Med. Bull. 22(5):181-194; Acta Allergol. 28:145-159, 1973).

*Primary Examiner*—Sidney Marantz
*Attorney, Agent, or Firm*—Mark A. Hofer; Geoffrey G. Dellenbaugh

[57] ABSTRACT

The method assesses the level of general and specific cellular immunocompetence by measuring the responses of individuals to antigens in vitro employing the phenomenon of Leukocyte Migration Inhibition (LMI). The present invention differs from the previously described LMI technique in that antigens are individually incorporated into the agarose of assay plates, requiring no preincubation of antigens with patient blood cell (leukocyte) suspensions. The LMI assay method described herein is a practical alternative to delayed hypersensitivity skin testing to identify cellular immune deficiency and avoids the risk and inconvenience of the skin test procedure. The method also allows in vitro diagnosis of Tuberculosis and monitoring of tumor therapy.

8 Claims, 4 Drawing Figures

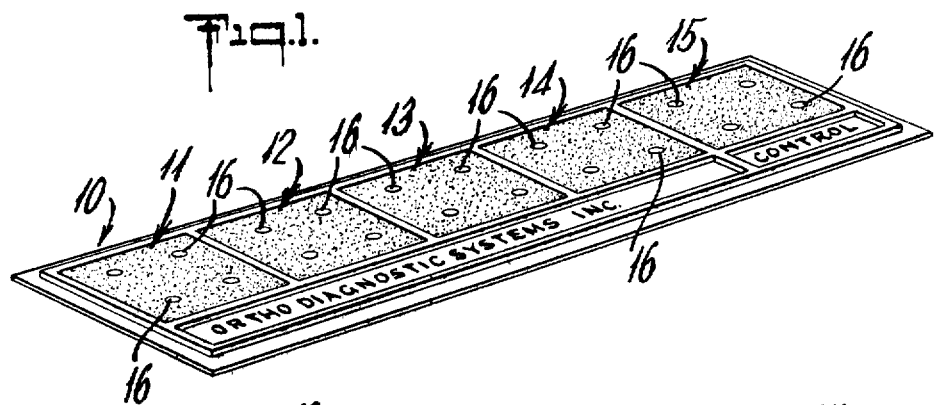
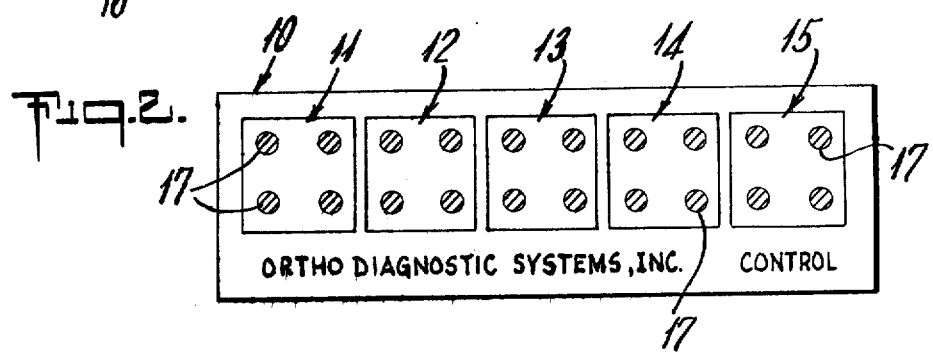
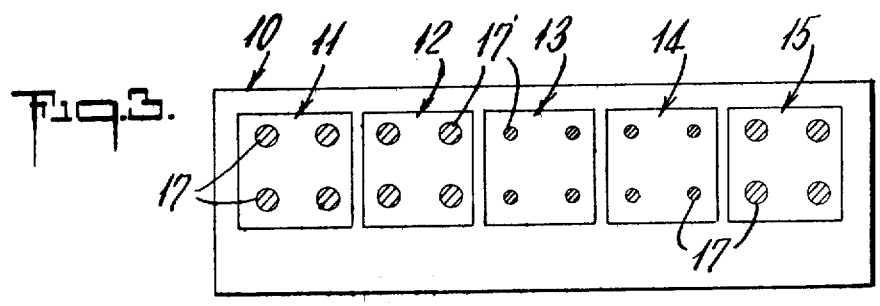
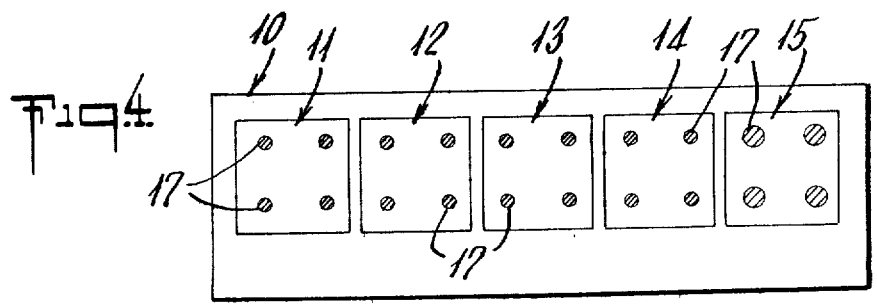

LEUKOCYTE MIGRATION THROUGH ANTIGEN CONTAINING AGAROSES FOR IMMUNOCOMPETENCE TESTING

FIELD OF THE INVENTION

The present invention relates generally to testing for immunocompetence and more specifically to an improved in vitro method for determining both general and specific immunocompetence employing the phenomenon of leukocyte migration inhibition.

BACKGROUND OF THE INVENTION AND PRIOR ART

Many diseases in humans are associated with diminished general cellular immune response or anergy. This defect is exhibited most prominently in congenital immunodeficiency diseases but also occurs in many patients with viral, bacterial, or fungal infections, as well as in so-called autoimmune diseases and cancer. Cellular immunodeficiency or anergy may also be induced by immunosuppressive therapy in the form of drug or radiation therapy. Regardless of the cause, the effect of this deficiency on the patient is a reduced ability to generate an adequate cellular immune response to invading organisms or "foreign" cells or tissues.

The most frequently used in vivo method for assessing cellular immunity in humans is delayed hypersensitivity skin testing. In this skin test, minute quantities of antigens are injected into the skin of the patient (intradermally), and the resultant reaction is measured at designated intervals after injection.

This delayed hypersensitivity skin reaction has a series of in vitro correlates which are understood to represent components or integral parts of the skin reaction. The in vitro tests measure the activity of one or more biological factors or kinins, also known as lymphokinins, and elicit responses from patient blood cells using the same antigens that are used in skin testing.

For determination of general cellular immunocompetence, the antigens used are so-called "recall" antigens, which are bacterial or viral extracts the use of which in the above-described in vivo and in vitro tests stems from the ability of normal individuals to remember or "recall" a cellular immune response due to sensitization early in life. Antigens most commonly used are tuberculin antigens (such as Purified Protein Derivative-Tuberculin (PPD)), Streptokinase-Streptodornase (SK-SD), Candida Albicans, Mumps, Tetanus Toxoid, Trichophyton, Histoplasmin, and Coccidiodin, but any other art-recognized recall antigen may be used.

With regard to tuberculin antigens in particular, it should be noted that there are a great number of these which have been extracted from or produced by the tubercle bacillus, including PPD, bacillus calmette Guerin (BCG), New tuberculin, Mantoux tuberculin, and the like. See, for example, the definition of "tuberculin" in Dorland's Medical Dictionary, 25th edition, W. B. Saunders, Philadelphia, 1974, for a list of common tuberculin antigen preparations.

At present, skin testing and in vitro assays employing "recall" antigens are used: (1) to determine anergy in selected patients, (2) to evaluate the results of immunotherapy for cancer and other diseases that have immunodeficiency as a major component, as either a cause or a result of the disease, (3) to monitor the severity of induced immunosuppression or (4) to follow the course of a disease process. It is well known that drug or radiation-induced suppression is an unavoidable byproduct of the treatment for many forms of cancer and the maintenance of organ transplant recipients. See, for example, L. E. Spitler, "Delayed Hypersensitivity Skin Testing" in *Manual of Clinical Immunology*, N. R. Rose and H. Friedman, et al., American Society of Microbiology, 1976.

Moreover, many tumors are characterized by specific immune responsiveness to the tumor antigens, which immune responsiveness is presently measured by a delayed hypersensitivity skin test as described above but with a tumor antigen substituted for the recall antigen. For many tumors, a correlation has been established between the degree of tumor specific immune response and the clinical state of the patient. A cellular immune response to a tumor-specific antigen in a tumor-bearing patient generally indicates a favorable clinical prognosis or outcome. After treatment of a patient by a variety of therapeutic techniques, a positive immune response in a patient who lacked such a response prior to treatment may be interpreted as a favorable prognosis and is correlated with disease remission. Conversely, a negative immune response in a patient who demonstrated a satisfactory response prior to treatment may be interpreted as an unfavorable prognosis and is not correlated with disease remission. Such skin tests may be used as evidence of an immune response to a tumor or tumor antigen, and may be used in conjunction with skin test employing "recall" antigens. See, for example, F. K. Nkrumah, et al., Int. J. Cancer: 20, 6–11 (1977) and D. H. Char, et al., N.E.J. Med: 291 (6), 274–277 (1974).

The prior art skin testing technique is well known to yield variable results due to differences in the dose of injected antigen, improper deposition of the antigen in the skin, instability of the antigen employed, and subjectivity involved in the reading of the reaction.

Moreover, skin testing is invasive and thus risks acute localized and systemic reactions in some individuals. This fact also makes skin testing unsuitable for repeated uses (e.g., monitoring) because repeated injections of antigen artificially boost the patient's immune response.

Finally, skin test procedures are not only associated with discomfort for the patient but also require reexamination of the patient 24 and 48 hours after testing to read the results. This necessity for observing the results is inconvenient, especially in a hospital setting (where weekends may intervene), which makes skin testing uncommonly used among outpatients.

Because skin testing has been known to involve these disadvantages and medical risks, recent efforts have focused on the use of the in vitro correlates for the above diagnostic purposes. The in vitro tests are noninvasive and do not risk acute systemic reactions (as are sometimes encountered with skin testing). In addition, these in vitro methods do not boost or artificially amplify the patient's immune response, as does the repeated use of skin tests.

Thus, only the in vitro methods are suitable for repeat testing that is needed to monitor patients who require potentially immunosuppressive therapy over time. These methods are less costly and safer than the skin test method. Unfortunately, however, no practical, portable in vitro test has been available in the past.

The present invention is based on the principle of Leukocyte Migration Inhibition (LMI). The basic elements of this cellular reaction were previously known. Lymphocytes obtained from patients who have been previously exposed (sensitized) to an antigen, upon reexposure to that antigen, elicit a defined protein factor referred to as Leukocyte Migration Inhibition Factor (LIF). This factor, which is one of a group of factors produced under the stated condition, causes the granulocytes from the same patient to be blocked or inhibited in movement (migration) in a variety of fluids or media. Inhibition of migration is interpreted as a positive, immunocompetent response to a given antigen. By using a variety of antigens, a profile is obtained to express the immune status of the patient at the time of testing.

Much of the previously known work on the LMI method is attributed to Clausen (Danish Med. Bull. 22(5):181–194; Acta Allergol. 28:145–158, 1973). He demonstrated that Leukocyte Migration Inhibition Factor (LIF) specifically causes inhibition of migration of granulocytes, can be measured in a direct, one stage test in agarose using peripheral blood lymphocyte-granulocyte mixtures or as a two-stage procedure in which cell free supernatant fluids (containing LIF) from antigen-stimulated lymphocyte cultures are assayed for migration inhibitory activity when added to purified leukocytes or granulocytes. Others have defined a relationship between the LMI method and delayed hypersensitivity skin testing (Astor and Fudenberg, J. Immunol. 110(4):1174, 1973).

The prior art LMI assay method requires the preincubation of a "recall" antigen at various concentrations with the leukocyte suspension from the patient and thus requires the fresh preparation of antigen and a mixing and incubation step prior to the test itself. Because of these features, the prior art LMI assay method requires specialized equipment and incubation of a cell suspension and hence is only slightly used. Specialized equipment often used in the prior art method includes, for example, a $CO_2$-perfused, temperature-controlled, water-jacketed 37° C. incubator and a binocular microscope equipped with a micrometer eyepiece. The preincubation requirement has prevented development of a convenient, portable test of broad general application.

The novel LMI method described herein uses individual antigens premixed in agarose slides or plates, at a single predetermined antigen concentration, requiring no antigen-cell preincubation to activate the lymphoid cells. Such a system is more rapid and reproducible, encourages standardization of the methodology, and has heretofore been unavailable.

That the subject LMI method works at all is most surprising in view of the results reported by Clausen in the above-described Acta Allergologica article. He attempted to perform an LMI assay in which the recall antigen (PPD) was mixed with the agarose used to prepare the assay plates, rather than being preincubated with the leukocytes. The reported results (beginning at the bottom of page 67 of the article) caused Clausen to conclude:

"Leukocytes from tuberculin-positive persons without the addition of PPD, cultured in agarose medium containing PPD showed *none, or only slight tuberculin induced migration inhibition,* but if the same leukocytes were preincubated with PPD and placed in a medium that did not contain PPD, the migration inhibition was seen clearly." (ibid, p. 75; emphasis added).

The described invention utilizes plates or slides containing agarose with a "recall" or tumor specific antigen incorporated into the agarose of each plate at a defined diagnostically effective concentration. Patient leukocytes are added directly to wells within the agarose, requiring no preincubation between antigens and cell suspensions prior to this addition.

SUMMARY OF THE INVENTION

The present invention provides methods and compositions for determining the level of cellular immunocompetence in a patient employing the phenomenon of leukocyte migration inhibition, which offers significant advantages over both the prior art LMI test and the prior art skin immunization technique.

In one aspect the present invention provides a method for determining the level of cellular immunocompetence in a patient which comprises the steps of:

(a) obtaining a sample of leukocytes from the patient;

(b) placing a leukocyte sample in at least one well of each of a plurality of antigen containing agarose sheets and one control agarose sheet;

(c) incubating the agarose sheets prepared in step (b);

(d) determining the amount of leukocyte migration from each well; and (e) determining the level of cellular immunocompetence of the patient from the amount of leukocyte migration determined in step (d);

wherein each of the plurality of antigen-containing agarose test sheets contains an effective diagnostic concentration of an individual recall antigen and the control agarose sheet contains no antigen.

In a second aspect the present invention provides a test kit for determining the level of cellular immunocompetence in a patient employing leukocyte migration inhibition which comprises a plurality of agarose sheets, each of said sheets containing an effective diagnostic concentration of an individual recall antigen and a control agarose sheet containing no antigen, all of said sheets being supported on a solid carrier and being provided with at least one well adapted to receive leukocyte samples.

Although it is contemplated that any agarose could serve in the present invention, several have been found to work particularly well. These are Induboise A-45 and A-37 agarose, manufactured by L'Industrie Biologique Francaise, 16 Boulevard du General Leclerc, 92115 Clichy, France, and available in the United States from Accurate Chemical and Scientific Corporation, Hicksville, N.Y. It is believed that agarose having an electroendosmosis number less than about 0.25 is preferred, this number being an indication of the proportion of charged particles in the agarose as determined by the rate at which ions move through the agarose in an electric field. However, this characteristic is not believed to be critical to the practice of the present invention.

Although it is expected that any group of recall antigens could be employed in the subject method or test kit, PPD, SK-SD, Candida Albicans, Mumps, Tetanus Toxoid, Trichophyton, Histoplasmin and Coccidiodin are a preferred group from which to select the recall antigens used.

Thus, the present invention provides for the first time a practical, portable test kit for in vitro determination of immunocompetence, free from the disadvantages which have plagued prior art tests. No incubation of the leukocyte samples with recall antigens is required prior to placing them in the wells of the agarose sheets. The present kits are standardized and simple to use, requiring no special equipment. Moreover, they offer greatly increased sensitivity compared to both the prior art Clausen assay and the prior art skin test method. There is also, of course, no necessity for the patient to make return visits to have the test "read" (as in skin testing), since the test is conducted in vitro.

In a further aspect of the present invention, it provides a method and test kit for in vitro detection of tuberculin reactivity. Prior art testing for tuberculin reactivity is conducted by means of the same sort of delayed hypersensitivity skin test described above. Sensitivity to PPD (the tuberculin antigen most commonly used in the United States) varies widely from region to region. As can be seen from the data presented in Example III below, most normal (immunocompetent) people in the New Jersey area show a negative reaction to PPD. It is for this reason that PPD is an unsuitable choice for a sole antigen in an LMI test, especially in regions of low sensitivity. In the prior art tuberculosis skin test, therefore, an additional recall antigen (e.g., Candida) is used as a positive control. A positive reaction to both PPD and Candida is strongly suggestive of tuberculosis infection, a negative reaction to both indicates lack of cellular immunocompetence, while a mixed reaction is inconclusive.

This further aspect of the present invention therefore provides an in vitro method for detecting tuberculin reactivity in a patient which comprises the steps of:

(a) obtaining a sample of leukocytes from the patient;

(b) placing a leukocyte sample in at least one well of each of three agarose sheets;

(c) incubating the agarose sheets prepared in step (b);

(d) determining the amount of leukocyte migration from each well; and (e) determining the presence or absence of tuberculin reactivity in the patient from the amount of leukocyte migration determined in step (d), wherein one of said agarose sheets contains an effective diagnostic concentration of a tuberculin antigen, the second agarose sheet contains no antigen, and the third agarose sheet contains a diagnostically effective concentration of an individual recall antigen other than a tuberculin antigen.

This further aspect of the present invention also provides a test kit for detecting tuberculin reactivity in a patient which comprises three agarose sheets, one of said sheets containing an effective diagnostic concentration of a tuberculin antigen, the second agarose sheet containing an effective diagnostic concentration of an individual recall antigen other than a tuberculin antigen, and the third agarose sheet containing no antigen; all of said sheets being supported on a solid carrier and being provided with at least one well adapted to receive leukocyte samples.

While it is believed that any tuberculin antigen preparation will be effective in the subject test, PPD, BCG, and Mantoux tuberculin are preferred.

In a still further aspect of the present invention, it provides a method and test kit for in vitro monitoring of the clinical state of a tumor patient by determining his level of tumor-specific cellular immunocompetence using tumor-specific antigens. Prior art testing for this characteristic has been carried out by the same sort of delayed hypersensitivity skin testing as described above, but employing tumor-specific antigens instead of recall antigens.

This still further aspect of the present invention thus provides a method for determining the level of tumor-specific immunocompetence in a patient which comprises the steps of:

(a) obtaining a sample of leukocytes from said patient;

(b) placing a leukocyte sample in at least one well of each of an antigen containing agarose sheet and a control agarose sheet;

(c) incubating the sheets;

(d) determining the amount of leukocyte migration from each well;

(e) determining the level of cellular immunocompetence of the patient based upon the amount of leukocyte migration in step (d), wherein the antigen-containing agarose test sheet contains an effective diagnostic concentration of an individual tumor-specific antigen and the control agarose sheet contains no antigen.

This still further aspect of the present invention also provides a test kit for determining the level of tumor-specific cellular immunocompetence in a patient employing leukocyte migration inhibition which comprises an agarose sheet containing an effective diagnostic concentration of an individual tumor-specific antigen and a control agarose sheet containing no recall antigen, each of said agarose sheets being supported on a solid carrier and being provided with at least one well adapted to receive samples of leukocytes.

The operation of the subject invention will be better understood by reference to the following Figures.

BRIEF DESCRIPTION OF THE DRAWINGS

FIG. 1 shows an assay plate of the present invention ready for use;

FIG. 2 shows an assay plate of the present invention after use, demonstrating a negative result (lack of immunocompetence);

FIG. 3 shows an assay plate of the present invention after use, demonstrating a partially positive result (immunocompetence); and FIG. 4 shows an assay plate of the present invention after use demonstrating a completely positive result (immunocompetence).

DETAILED DESCRIPTION OF THE INVENTION

A typical assay plate (10) useful in the practice of the present method is shown in FIG. 1, the plate (10) being segmented into four assay areas containing four agarose sheets (11, 12, 13, 14) each having an individual recall (or tumor specific) antigen mixed therein and one control agarose sheet (15) having no antigen. Each sheet is provided with four wells (16), although this number is not critical.

In the practice of the subject invention, each of the wells (16) is filled with leukocyte suspension, the plate is incubated, and the results are read by observing the area (17) of the leukocyte migration in the antigen-containing sheets compared to that in the control sheet. To eliminate chance variabilities, the results for the four wells in each sheet are averaged and the averages are compared. The area of leukocyte migration can readily be determined by removing the agarose from the plate and measuring the resulting circles of leukocytes on the bottom of the plate. Conveniently, this may be done using a transparent score card having a succession of dark circles of increasing area, superimposing each circle over the area to be determined until congruence is obtained, and reading the area off the card.

FIGS. 2–4 show typical results of the subject invention.

FIG. 2 shows results for an immunocompetent person (i.e., "negative" results). No inhibition was caused (compared to the control) for any of the four recall antigens employed, as shown by the fact that areas (17) are the same for antigen-containing sheets and the control sheet.

FIG. 3 shows results for an immunocompetent person (i.e., partially "positive" results). Inhibition of leukocyte migration was caused by certain of the recall antigens, yielding reduced areas (17) in those sheets, but not by others. This result is interpreted as positive even though migration did not occur with all recall antigens, which points up the necessity of using a panel of antigens in the subject test. A positive reaction (inhibition) to any one of the recall antigens employed demonstrates that the patient's immune system reacted to it and is therefore competent. This criterion for cellular immune competence has been generally applied to the evaluation of skin test reactions. (See Palmer, D. L. and W. P. Reed, J. Infect. Dis. 130:132, 1974). Failure to react to some (but not all) antigens, on the other hand, cannot be due to a general immune deficiency but rather to some specific antigen-related effect.

Finally, FIG. 4 shows completely positive results, in that all of the recall antigens employed caused inhibition as indicated by reduced areas (17) in the antigen-containing sheets.

Similar results would be obtained employing tumor-specific antigens instead of or in addition to recall antigens. Thus, if sheets (13-14) of FIG. 3 contained individual tumor-specific antigens instead of individual recall antigens, this Figure would show absence of an immune response to the two individual tumor antigens in the individual being screened. This conclusion would be supported by the positive results for sheets (11-12) containing recall antigens, which function as a positive control to demonstrate cellular immunocompetence in general. Therefore, the negative results with sheets (13-14) may properly be interpreted as lack of sensitization to the tested tumor antigens.

If these results were obtained in a patient previously reactive to one or both of these tumor antigens, these results would be interpreted as signifying a less favorable prognosis. Contrarywise, if an immune response were obtained in a previously unresponsive patient after treatment, that result would imply a more favorable prognosis.

Of course, any antigen of demonstrated tumor specificity may be used, depending upon the tumor for which the test is being conducted.

The present invention is further described by the following Examples, which are provided by way of illustration and not to limit the subject invention.

EXAMPLE I—GENERAL PROCEDURE

Approximately 10 ml of venous blood is collected from each patient, and the blood is made non-coagulating by the addition of phenol-free heparin or ethylenediaminetetraacetic acid (EDTA). Each blood sample is added to a tube containing dextran (Dextran T500, Pharmacia Fine Chemicals, Piscataway, N.J.) at a concentration of 6% W/V in normal saline (0.85% sodium chloride). A ratio of four parts of anticoagulated blood to one part of 6% dextran is most appropriate. The blood-dextran mixture is allowed to stand upright at 37° C. for one hour or at ambient temperature (25° C.) for 90 minutes to allow sedimentation of erythrocytes. The entire blood-dextran supernate is then removed by an appropriate pipette and transferred to a 50 ml centrifuge tube, discarding the lower red cell layer. The tube is filled with Hanks Balanced Salt Solution (HBSS) and centrifuged at a speed of $500 \times g$ for 10 minutes at room temperature. The supernatant fluid is decanted. The remaining leukocyte pellet is suspended in HBSS, after which the centrifugation is repeated to eliminate the dextran. The leukocyte pellet is again suspended in 0.1 ml of medium 199 with HBSS, (Grand Island Biological Company, Grand Island, N.Y.) containing 10% W/V of heat-inactivated horse serum. Alternatively, leukocytes in the suspension are enumerated by standard techniques and suspended to a concentration of $2.4 \times 10^8$/ml. This leukocyte preparation is referred to herein as the "leukocyte suspension".

Agarose medium containing recall antigen is prepared as follows: to prepare 100 ml amounts of agarose, 1.1 grams of agarose (Induboise-A45 or A-37, Accurate Chemical and Scientific Corporation, Hicksville, N.Y.) is dissolved in 50 ml of distilled water and boiled for 10 minutes with careful stirring. After boiling, the volume is readjusted to 50 ml to compensate for evaporative loss. Forty-five ml of 2X medium 199 with HBSS containing 20 mM HEPES buffer (Calbiochem-Behring Corporation, La Jolla, Calif.), 200 µg/ml of Gentamycin and 100 µg/ml of Fungizone are added to an equal volume of the above agarose solution. The combined preparation above is referred to herein as "agarose medium". The agarose medium is held at 48°–50° C. until assay plates are poured. "Recall" antigens are added individually to amounts of agarose medium to achieve the desired final concentration. This is best done by preparing working diluents of antigens in sterile normal saline (0.85% sodium chloride) at 10 times the final concentration desired in the assay. For example, PPD is prepared and added to agarose medium at a concentration of 1 mg/ml so as to achieve a final concentration of 100 µg/ml. SK-SD is prepared at 1000 units/ml to achieve a final concentration of 100 units/ml. The appropriate concentration of each recall antigen may be readily determined by, for example, preparing a dose-response curve. The term "diagnostically effective concentration" of antigen includes any concentration of a given antigen which permits discrimination between positive and negative subjects.

For the purpose of comparison of the subject invention with the prior art preincubation method, the above antigens may be preincubated with leukocyte suspension at various antigen and leukocyte concentrations, according to the method of Clausen (Danish Med. Bull. 22(5):181–194, 1975). In this procedure, 20 µl of a recall antigen is added to 180 µl of leukocytes suspended to a concentration of $2.4 \times 10^8$/ml and incubated at 37° C. for 30 minutes before addition of the leukocytes to assay plates. This leukocyte preparation is referred to herein as the "preincubated leukocyte suspension".

To prepare the assay plates, 4 ml of agarose medium to which one of the recall antigens has been added (or not added in the case of control plates or prior art comparison) is pipetted into Immunoplates (Hyland Labs., Costa Mesa, Calif.), and allowed to set at room temperature. A control plate containing agarose medium without antigen is prepared for each set of antigen-containing plates. Four 2 mm diameter wells are punched into the solidified agarose of each plate and the agarose plug is removed by suction. Punched plates with tight-fitting lids are stored at 4° C. until used for the assay.

To conduct the assay, 4 μl of the leukocyte suspension prepared above is added to each well of each agarose-containing plate. Ideally, the test panel for each donor consist of five plates; one control plate to exhibit normal migration of cells in the absence of antigen and one plate for each of four recall antigens. However, it should be understood that the precise number of plates used is by no means critical. Prepared plates with firmly attached lids may be placed in zip-lock plastic bags to prevent moisture loss, and incubated for approximately 16 hours at 37° C. in a moist atmosphere. Assay plates are subsequently removed from the bags, the agarose crosslinked with 3.0% glutaraldehyde and removed, and the area of cell migration on the plate is measured for each well of each plate with a scoring card. The agarose is conveniently removed to facilitate measurement of the area of leukocyte migration (which occurs along the surface of the plate under the agarose) but is not an essential feature of the present invention.

A migration Index (M.I.) is obtained for each "recall" antigen tested on a given donor, as follows:

$$M.I. = \frac{\text{Mean Migration Area of Leukocytes in the Presence of a ``Recall'' Antigen}}{\text{Mean Migration Area of Leukocytes in the Absence of a ``Recall'' Antigen}}$$

In practice, the donor's response to a given antigen is considered to be positive (and hence immunocompetent) if the leukocytes are inhibited in migration by 20% or more of the migration obtained without antigen, i.e., an M.I. value of 0.80 or less.

The utility of the described invention may be demonstrated by: (1) Comparison with previously known in vitro methods that are based on the principle of Leukocyte Migration Inhibition (LMI) as an indicator of cellular immune responsiveness, or (2) Comparison with delayed hypersensitivity skin testing as an indicator of cellular immune responsiveness.

The first prior art demonstration of the LMI reaction made use of capillary tubes filled with liquid medium. The method was applied to tuberculin positive individuals to exhibit tuberculin-specific inhibition of migration of leukocytes (Soborg and Bendixen, Acta Med. Scand. 186:227–230, 1967). The superior properties of a solid support to exhibit cell migration, such as agarose, was subsequently demonstrated (Clausen, Acta Allergol. 56–80, 1971).

Prior to the present invention, all methods for demonstrating the reaction required incubation of leukocytes from previously sensitized donors with a recall antigen to obtain a positive response. Moreover, the method was exhibited essentially for the purpose of measuring responses to PPD.

EXAMPLE II—COMPARISON WITH PRIOR ART IN VITRO ASSAYS

By comparison to the practice of the present invention, leukocyte suspensions were obtained from normal blood donors and preincubated with various recall antigens at various antigen and cell concentrations. When the prior art in vitro method of Clausen is compared carefully to the present invention, it is revealed that both methods are comparable for measuring responses to PPD, but only the present invention, utilizing recall antigens in agarose, is sufficiently sensitive to measure responses to other "recall" antigens employed. These antigens are, for example, SK-SD, Candida, Staphage, Mumps, Coccidiodin and Histoplasmin.

EXAMPLE III—COMPARISON WITH DELAYED HYPERSENSITIVITY SKIN TESTING

The utility of the present invention is best demonstrated by a comparison of the invention with skin testing on the same normal or diseased individuals, using the same "recall" antigens. In this demonstration, the antigens PPD, SK-SD, Candida, and Tetanus were used at concentrations that are appropriate to the respective test protocols. The generally accepted procedure for skin testing (Spiller, Man. of Clin. Immunol., Pub. American So. for Microbiology, pg 53–63, 1976, and Astor, et al., J. Immunol. 110(4):174–1179, 1973) indicates that antigens may be first used at intermediate strengths, followed by a second (higher) strength if the intermediate strength is negative. The data from these comparative tests are given below:

(1) Normal Data

| Results | Antigen Subject Test | Skin Test | % Correlation | P |
|---|---|---|---|---|
| | PPD | | | |
| positive | 1 | 0 | 90.9 | <0.01 |
| negative | 10 | 11 | | |
| | SK-SD | | | |
| positive | 7 | 7 | 100.00 | <0.01 |
| negative | 0 | 0 | | |
| | Candida | | | |
| positive | 11 | 11 | 100.00 | <0.01 |
| negative | 0 | 0 | | |
| | Tetanus | | | |
| positive | 9 | 8 | 90.9 | <0.01 |
| negative | 2 | 3 | | |

The analysis indicates that the subject method yields results which are statistically identical to the prior art skin test at a significant level of probability.

One may more readily appreciate "% Correlation" if one presumes that the skin test is correct (or true). The % Correlation value thus represents true positive plus true negative data and excludes false positive and false negative data. The average % correlation for the four antigens tested on normal donors is 95.5%.

(2) Patient Data

| Results | Antigen Subject Test | Skin Test | % Correlation | P |
|---|---|---|---|---|
| | PPD | | | |
| positive | 3 | 4 | 87.5 | <0.01 |
| negative | 37 | 36 | | |
| | SK-SD | | | |
| positive | 32 | 30 | 93.8 | <0.01 |
| negative | 0 | 2 | | |
| | Candida | | | |
| positive | 41 | 38 | 88.1 | <0.01 |
| negative | 1 | 4 | | |

The average % correlation for the above patient data is 89.8%.

Although the study was small and limited to a single study site, a statistically valid conclusion can be drawn, namely that the subject test is essentially equivalent to the prior art skin test for both patients and normal donors. Although only four antigens were tested in this comparison, other recall antigens would show a similar correlation when skin tested.

While the present invention has been illustrated by the above Examples, it should be understood that the scope of invention is not to be limited thereto but is as defined in the appended claims.

What is claimed is:

1. A method for determining the level of cellular immunocompetence in a patient which comprises the steps of:
    (a) obtaining a sample of leukocytes from said patient;
    (b) placing a leukocyte sample, with substantially no prior incubation with antigen, in at least one well of each of a plurality of antigen-containing agarose sheets and one control agarose sheet;
    (c) incubating the sheets;
    (d) determining the amount of leukocyte migration from each well; and
    (e) determining the level of cellular immunocompetence of the patient based upon the amount of leukocyte migration in step (d),
wherein each of the plurality of antigen-containing agarose test sheets contains an effective diagnostic concentration of an individual recall antigen and the control agarose sheet contains no antigen.

2. The method of claim 1 wherein the recall antigens are selected from the group consisting of PPD, SK-SD, Candida Albicans, Mumps, Tetanus Toxoid, Trichophyton, Histoplasmin, and Coccidiodin.

3. A method for detecting tuberculin reactivity in a patient which comprises the steps of:
    (a) obtaining a sample of leukocytes from the patient;
    (b) placing a leukocyte sample, having substantially no prior incubation with antigen, in at least one well of each of three agarose sheets;
    (c) incubating the agarose sheets prepared in step (b);
    (d) determining the amount of leukocyte migration from each well; and
    (e) determining the presence or absence of tuberculin reactivity in the patient from the amount of leukocyte migration determined in step (d),
wherein one of said agarose sheets contains an effective diagnostic concentration of a tuberculin antigen, the second agarose sheet contains a diagnostically effective concentration of an individual recall antigen other than a tuberculin antigen, and the third agarose sheet contains no antigen.

4. The method of claim 3 wherein the tuberculin antigen is selected from the group consisting of PPD, BCG, and Mantoux tuberculin.

5. A test kit for detecting tuberculin reactivity in a patient which comprises three agarose sheets, one of said sheets containing an effective diagnostic concentration of a tuberculin antigen, the second of said sheets containing an effective diagnostic concentration of an individual recall antigen other than a tuberculin antigen, and the third of said sheets containing no antigen; each of said sheets being supported on a solid carrier and being provided with at least one well adapted to receive leukocyte samples.

6. The test kit of claim 5 wherein the tuberculin antigen is selected from the group consisting of PPD, BCG, and Mantoux tuberculin.

7. A method for determining the level of tumor-specific cellular immunocompetence in a patient which comprises the steps of:
    (a) obtaining a sample of leukocytes from said patient;
    (b) placing a leukocyte sample having substantially no prior incubation with tumor-specific antigens, in at least one well of each of an antigen containing agarose sheet and a control agarose sheet;
    (c) incubating the sheets;
    (d) determining the amount of leukocyte migration from each well;
    (e) determining the level of tumor-specific cellular immunocompetence of the patient based upon the amount of leukocyte migration in step (d),
wherein the antigen-containing agarose test sheet contains an effective diagnostic concentration of an individual tumor-specific antigen and the control agarose sheet contains no antigen.

8. A test kit for determining the level of tumor-specific cellular immunocompetence in a patient employing leukocyte migration inhibition which comprises an agarose sheet containing an effective diagnostic concentration of an individual tumor-specific antigen and a control agarose sheet containing no antigen, each of said agarose sheets being supported on a solid carrier and being provided with at least one well adapted to receive samples of leukocytes.

* * * * *